United States Patent
Fang et al.

(10) Patent No.: US 7,936,911 B2
(45) Date of Patent: May 3, 2011

(54) 3D PLANNING AND PREDICTION METHOD FOR OPTIMIZING FACIAL SKELETON SYMMETRY IN ORTHOGNATHIC SURGERY

(75) Inventors: Jing-Jing Fang, Tainan (TW); Tung-Yiu Wong, Tainan (TW)

(73) Assignee: National Cheng Kung University, Tainan (TW)

( * ) Notice: Subject to any disclaimer, the term of this patent is extended or adjusted under 35 U.S.C. 154(b) by 202 days.

(21) Appl. No.: 12/479,111

(22) Filed: Jun. 5, 2009

(65) Prior Publication Data
US 2009/0311647 A1    Dec. 17, 2009

(30) Foreign Application Priority Data
Jun. 11, 2008 (TW) .............................. 97121637 A

(51) Int. Cl.
G06K 9/00 (2006.01)

(52) U.S. Cl. ........................................ 382/128; 382/154

(58) Field of Classification Search .................. 382/128, 382/129, 130, 131, 132, 154; 128/922; 345/419
See application file for complete search history.

(56) References Cited

U.S. PATENT DOCUMENTS
7,801,345 B2 *  9/2010  Fang et al. .................... 382/128
* cited by examiner

*Primary Examiner* — Brian Q Le
(74) *Attorney, Agent, or Firm* — patenttm.us

(57) ABSTRACT

The method comprises steps of making a plaster dental cast of a patient, reconstructing jaw image assembly models, performing registration between physical stone and image model, adjusting the plaster dental cast based on a x-ray cephalometric plan, tracking movements of the plaster dental cast, obtaining optimal symmetry planes of the upper and lower jaw image assemblies, determining whether a degree of overall symmetry is elevated, and making surgical occlusal splints for surgical guiding. With foregoing method, possible results of executing an orthognathic surgical plan can be predicted and the surgical plan can be considered more carefully to achieve both occlusion function and facial symmetry.

12 Claims, 17 Drawing Sheets

3D PLANNING AND PREDICTION METHOD FOR OPTIMIZING FACIAL SKELETON SYMMETRY IN ORTHOGNATHIC SURGERY

BACKGROUND OF THE INVENTION

1. Field of the Invention

The present invention relates to a method for planning orthognathic surgery, especially relates to a 3D planning and prediction method for optimizing facial skeleton symmetry in orthognathic surgery.

2. Description of the Related Art

Orthognathic surgery is commonly practiced in oral and maxillofacial region. Such surgery is performed to correct positions of jawbones with asymmetric facial structure, severe skeletal discrepancy or orthodontic problems. Before performing an orthognathic surgery, a surgeon first diagnoses oral and maxillofacial problems of the patient, then makes a pre-surgical plan with 2-D cephalometric analysis and performs the orthognathic surgery accordingly. Based on the pre-surgical plan, jawbones of the patient may be segment and re-aligned in a predetermined position. If the pre-surgical plan is not carefully made, the surgery may not have a predicted treatment effect on the patient.

When making a pre-surgical plan for an orthognathic surgery, cephalometric x-ray images of the patient's head in front and lateral directions will be taken by a surgeon to determine a two-dimensional post-surgical target position of jawbones by using transparent tracing paper with feature lines of jawbone edges. A plaster dental cast including upper and lower jaws will be made according to the patient's oral cavity. The plaster dental cast is provided for the surgeon to simulate the orthognathic surgery according to the target position of jawbones to show a possible post-surgical appearance of jaws before putting the surgery into practice. However, because of the lack of three-dimensional information, such as rotation angles of jaws, post-surgical relation between the positions of upper and lower jaws cannot be precisely predicted by the cephalometric x-ray photos and the surgeon's experiences. Therefore the orthognathic surgery may lead to a result that dental occlusion is correct but facial appearance is still asymmetric.

In conclusion, a pre-surgical plan made by foregoing traditional method has disadvantages as follows:

1. Positions of teeth and jaws cannot be simultaneously considered, the post-surgical result often leads to perfect dental occlusion with asymmetric jaws.

2. Try-and-error adjustment of two-dimensional cephalometry transferred to the dental cast is time-consuming and is difficult to satisfy both occlusion function and facial aesthetic.

3. Two-dimensional cephalometry combined with substantial plaster dental cast cannot provide rotation angles of jaws in three-dimensional space.

4. Taking rest occlusion as a prior consideration to x-ray cephalometry is difficult to achieve substantial facial skeleton symmetry.

To overcome the shortcomings, the present invention provides a 3D planning and prediction method for optimizing facial skeleton symmetry in orthognathic surgery to mitigate or obviate the aforementioned problems.

SUMMARY OF THE INVENTION

The main objective of the invention is to provide a 3D planning and prediction method for optimizing facial skeleton symmetry in orthognathic surgery.

The 3D planning and prediction method for optimizing facial skeleton symmetry in orthognathic surgery in accordance with the present invention comprises steps of:

making a plaster dental cast according to an oral cavity of a patient, wherein the plaster dental cast has an upper jaw stone assembly and a lower jaw stone assembly;

reconstructing jaw image assembly models in a computer by scanning the patient's facial structure using computer tomography, wherein the jaw image assembly models include an upper jaw image assembly and a lower jaw image assembly;

performing registration between the jaw image assembly models and the plaster dental cast, wherein a coordinate relationship between the virtual jaw image assembly models and the substantial plaster dental cast is established in the computer by coordinate transformation for position synchronization;

adjusting positions of the upper and lower jaw stone assemblies of the plaster dental cast to target positions according to a predetermined x-ray cephalometric plan;

tracking movements of the upper and low jaw stone assemblies with a spatial tracking device to synchronously and correspondingly reappear the same movements of the upper and lower jaw image assemblies to obtain a relative variation between positions of the upper and lower jaw image assemblies;

obtaining optimal symmetry planes of the upper and lower jaw image assemblies by a computer via an asymmetry quantifying process and thereby computing a variation of an included angle and a specific distance between the optimal symmetry planes of the upper and lower jaw image assemblies;

determining whether a degree of overall symmetry is elevated by determining whether the included angle and the specific distance are shortened under a condition of compromising the x-ray cephalometric plan, and recording the included angle and the specific distance and proceeding to next step when the degree of overall symmetry is elevated, otherwise checking if any error occurs while adjusting positions of the upper and low jaw stone assemblies of the plaster dental cast according to the x-ray cephalometric plan and returning to the step of tracking movements of the upper and low jaw stone assemblies of the plaster dental cast; and making surgical occlusal splints according to the x-ray cephalometric plan and the recorded included angle and specific distance for surgical guiding.

With foregoing method, possible results after executing a surgical plan of an orthognathic surgery can be considered more carefully to achieve both occlusion function and facial symmetry.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
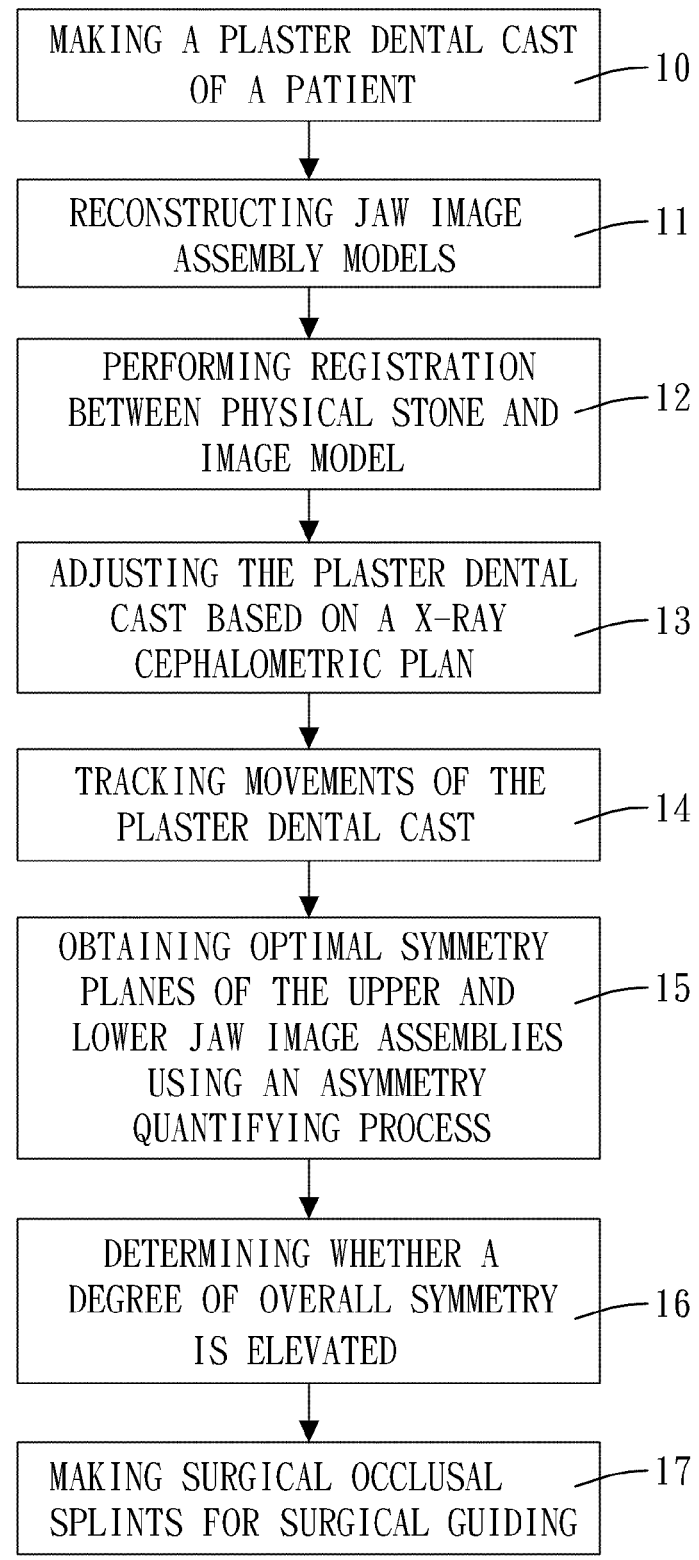
FIG. 1 is a flow chart of a preferred embodiment of a 3D planning and prediction method for optimizing facial skeleton symmetry in orthognathic surgery in accordance with the present invention.

Refer to FIG. 1, a 3D planning and prediction method for optimizing facial skeleton symmetry in orthognathic surgery in accordance with the present invention comprises steps of making a plaster dental cast of a patient (10), reconstructing jaw image assembly models (11), performing registration between physical stone and image model (12), adjusting the plaster dental cast based on a x-ray cephalometric plan (13), tracking movements of the plaster dental cast (14), obtaining optimal symmetry planes of the upper and lower jaw image assemblies using an asymmetry quantifying process (15), determining whether a degree of overall symmetry is elevated (16), and making surgical occlusal splints for surgical guiding (17).

The step of making a plaster dental cast of a patient (10) comprises making a plaster dental cast according to an oral cavity of a patient. The plaster dental cast has an upper jaw stone assembly and a lower jaw stone assembly.

The step of reconstructing jaw image assembly models (11) comprises scanning the patient's facial structure by computer tomography to reconstruct 3D jaw image assembly models in a computer. The jaw image assembly models comprise an upper jaw image assembly and a lower jaw image assembly.

The step of performing registration between physical stone and image model (12) comprises performing registration between the jaw image assembly models and the plaster dental casts to make the jaw image assembly models coincide with the plaster dental cast, wherein a coordinate relationship between the virtual jaw image assembly models and the substantial plaster dental casts is established in the computer by coordinate transformation for position synchronization.

The step of adjusting the plaster dental cast based on a x-ray cephalometric plan (13) comprises adjusting positions of the upper and lower jaw stone assemblies of the plaster dental cast to target positions according to a predetermined x-ray cephalometric plan. The x-ray cephalometric plan is created in advance by a surgeon with two-dimensional cephalometric analysis. Each jaw stone assembly may maintain complete or may be cut into at least one jawbone piece due to different surgical cases. For example, the upper jaw stone assembly may be cut into a left jawbone piece and a right jawbone piece.

The step of tracking movements of the plaster dental cast (14) comprises tracking movements of the upper and lower jaw stone assemblies of the plaster dental cast by a spatial tracking device to synchronously and correspondingly reappear the same movements of the upper and lower jaw image assemblies of the jaw image assembly models to obtain a relative variation between positions of the upper and lower jaw image assemblies of the jaw image model. The spatial tracking device may be an optical tracking device, a mechanical tracking device, an ultrasonic tracking device, a gyroscope tracking device, an electromagnetic tracking device or other tracking devices.

The step of obtaining optimal symmetry planes of the upper and lower jaw image assemblies using an asymmetry quantifying process (15) comprises obtaining optimal symmetry planes of the upper and lower jaw image assemblies by a computer via an asymmetry quantifying process and thereby computing a variation of an included angle and a specific distance between the optimal symmetry planes of the upper and lower jaw image assemblies of the jaw image models. The specific distance is defined as a shortest distance from a lowest position of the optimal symmetry plane of the lower jaw image assembly to the optimal symmetry plane of the upper jaw image assembly.

The step of determining whether a degree of overall symmetry is elevated (16) comprises determining whether a degree of overall symmetry is elevated by determining whether the included angle and the specific distance are shortened under a condition of compromising the x-ray cephalometric plan. If yes, record the included angle and the specific distance and proceed to next step. If not, check if any error occurs when adjusting positions of upper and lower jaw stone assemblies of the plaster dental cast according to the x-ray cephalometric plan and return to step (14).

The step of making surgical occlusal splints for surgical guiding (17) comprises making surgical occlusal splints on the plaster dental cast according to the x-ray cephalometric plan and the recorded included angle and specific distance for surgical guiding.

Figure 2:
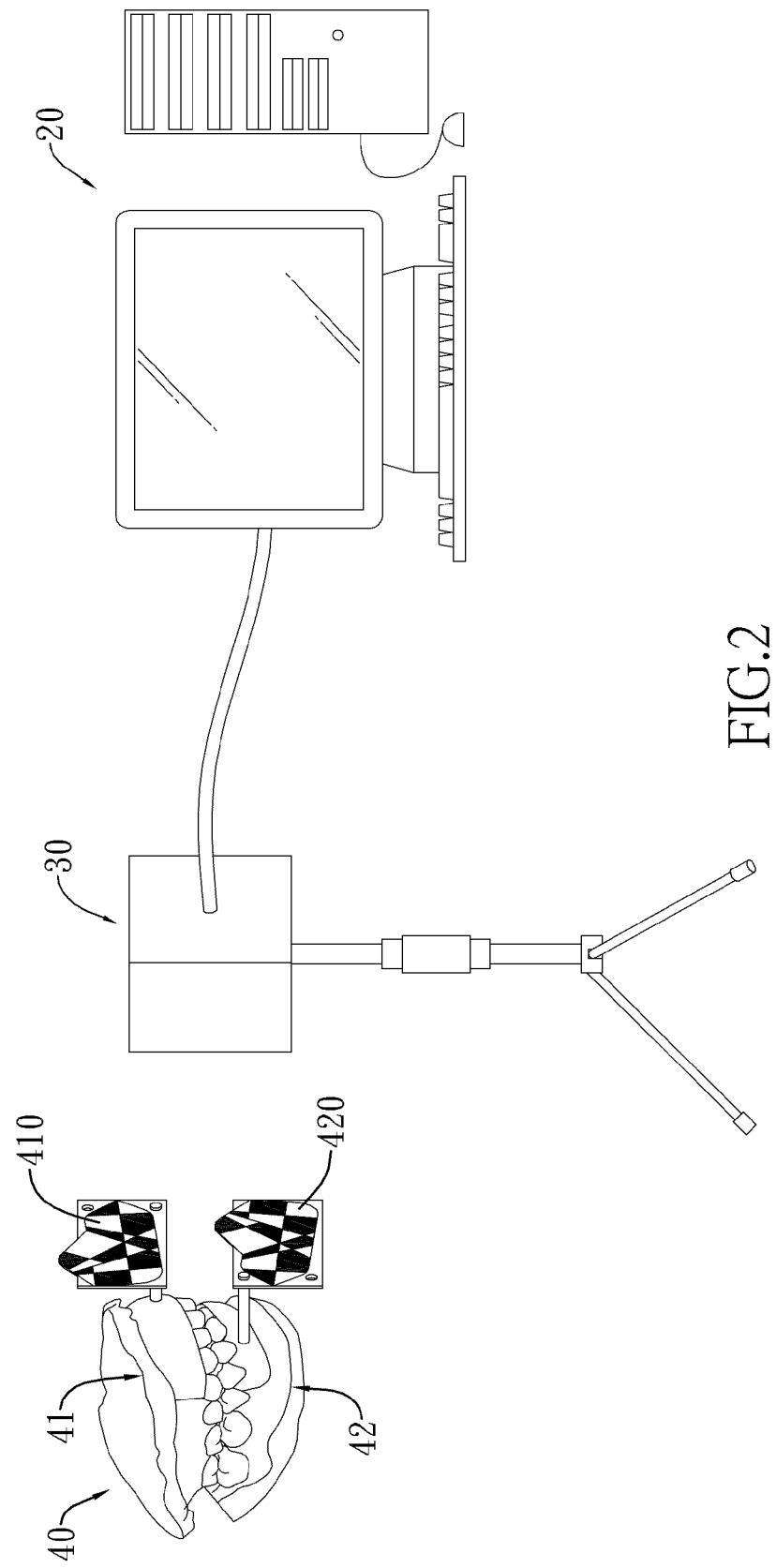
FIG. 2 is an operational scheme when executing a step of tracking spatial positions of upper and lower jaw stone assemblies of a plaster dental cast.

With further reference to FIG. 2, executing the step of tracking movements of the upper and lower jaw stone assemblies of the plaster dental casts (14) may require a computer (20) and an optical tracking device (30). The optical tracking device (30) is connected to the computer (20) and faces plaster dental casts (40). Preferably the plaster dental casts (40) have an upper jaw stone assembly (41), a lower jaw stone assembly (42) and multiple tracking plates (410, 420). The tracking plates (410, 420) are respectively mounted on the upper jaw stone assembly (41) and the lower jaw stone assembly (42) as tracking guide of the optical tracking device (30).

Each tracking plate (410, 420) may have at least three recognition spots or two vector-based patterns, such as being attached with light-emitting diodes, reflection balls or recognized patterns as tracking targets for spatial coordinate establishment. Preferably each tracking unit (410, 420) is painted alternatively with black and white to have an irregular pattern as shown in FIG. 2. The optical tracking device (30) can build a spatial coordinate system based on the irregular patterns of the tracking units (410, 420). When adjusting positions of upper and lower jaw stone assemblies (41, 42) of the plaster dental casts (40), the optical tracking device (30) then tracks movements of the tracking units (410, 420) of the upper and lower jaw stone assemblies (41, 42) and sends image data to the computer (20). The computer (20) then calculates displacements of the upper and lower jaw stone assemblies (41, 42) based on the received image data and simultaneously corresponds to foregoing jaw image assembly models. The jaw image assembly models accordingly perform the same movement simultaneously.

The upper and lower jaw stone assemblies (41, 42) of the plaster dental casts (40) may further be cut into smaller pieces due to surgical requirements. For example, the upper jaw stone assembly may be cut into two pieces, a midface piece and a maxilla piece, and the lower jaw stone assembly may be cut into three pieces, a mandible body piece, a left mandible ramus, and a right mandible ramus piece.

Figure 3:
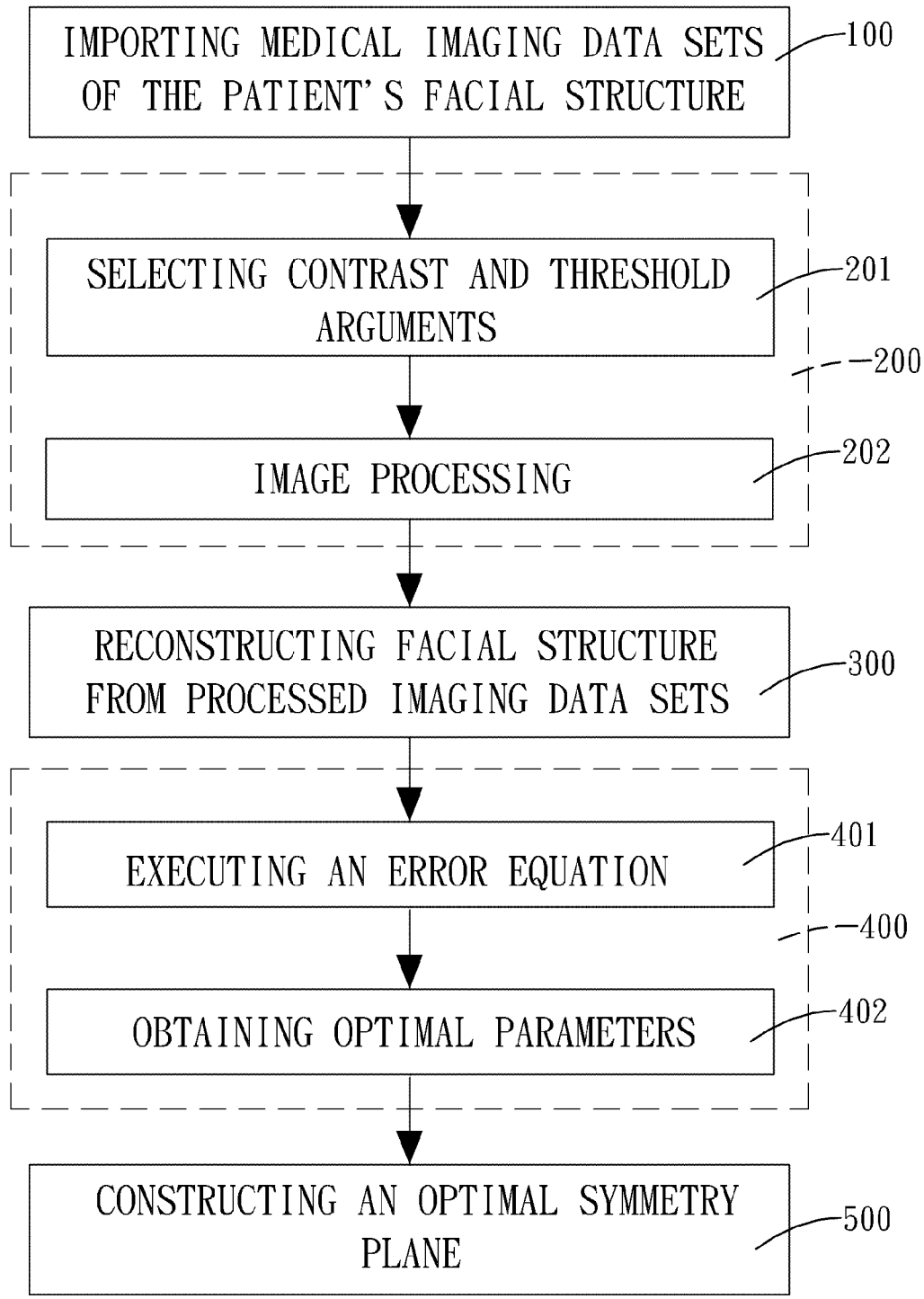
FIG. 3 is a flow chart of a first embodiment of an asymmetry quantifying process.

With further reference to FIG. 3, aforementioned the asymmetry quantifying process can be referred to the U.S. patent application Ser. No. 11/580,594, filed on Oct. 13, 2006, entitled "Method of Quantifying Asymmetry of an Object". The asymmetry quantifying process is performed in a computer and comprises steps of importing medical imaging data sets of the patient's facial structure (100), selecting regions of interest of the patient's facial structure in each medical imaging data set (200), reconstructing facial structure from processed imaging data sets (300), executing an error function to obtain optimal parameters for optimal symmetry plane (400) and constructing an optimal symmetry plane (500).

The step of importing multiple medical imaging data sets of the patient's facial structure (100) comprises importing medical imaging data sets of the patient's facial structure into a computer. Each imaging data set comprises multiple image data. In an embodiment of the present invention, the medical imaging data sets are captured by computer tomography and are integrated into said jaw image assembly models.

The step of selecting regions of interest (ROI) of the patient's facial structure in each medical imaging data set (200) locates the regions of interest of the patient's facial structure in each medical imaging data set and comprises steps of selecting contrast and threshold arguments (201) and then image processing (202).

The contrast and threshold arguments relate to gray scale gradations of the image data. For example, suppose pixels or voxels of a 2-D or 3-D imaging data set obtained by Computer Tomography have 4096 gray level, and further, the gray level of human bone in the image data may be within the range of 1323-4095. Therefore, the contrast and threshold arguments used in determining human bone are in the range of 1323-4095.

The step of image processing (202) uses the contrast and threshold arguments to generate binary image data and locates the regions of interest of the patient's facial structure in each medical image data set.

The step of reconstructing facial structure from processed imaging data sets (300) comprises region growing in the regions of interest by connecting neighbor layer of medical images.

The step of processing the medical image data in each data set (400) comprises steps of executing an error equation (401) and obtaining optimal parameters (402).

The error equation and the optimal parameters are obtained as follows:

1. $f(x, y, z)$ is a gray level equation of the patient's facial structure in the medical, and $E(x, y, z)=ax+by+cz+d=0$ is assumed to be a symmetry plane equation in the jaw image model.

2. A pixel's coordinates are $(x_i, y_i, z_i)$ and the pixel's symmetric coordinates assumed to relate to the symmetry plane are $(x_{si}, y_{si}, z_{si})$. Therefore $$x_{si} = x_i - \frac{2a}{\sqrt{a^2+b^2+c^2}}(ax_i + by_i + cz_i + d),$$

$$y_{si} = y_i - \frac{2b}{\sqrt{a^2+b^2+c^2}}(ax_i + by_i + cz_i + d)$$

and $$z_{si} = z_i - \frac{2c}{\sqrt{a^2+b^2+c^2}}(ax_i + by_i + cz_i + d).$$

Figure 4:
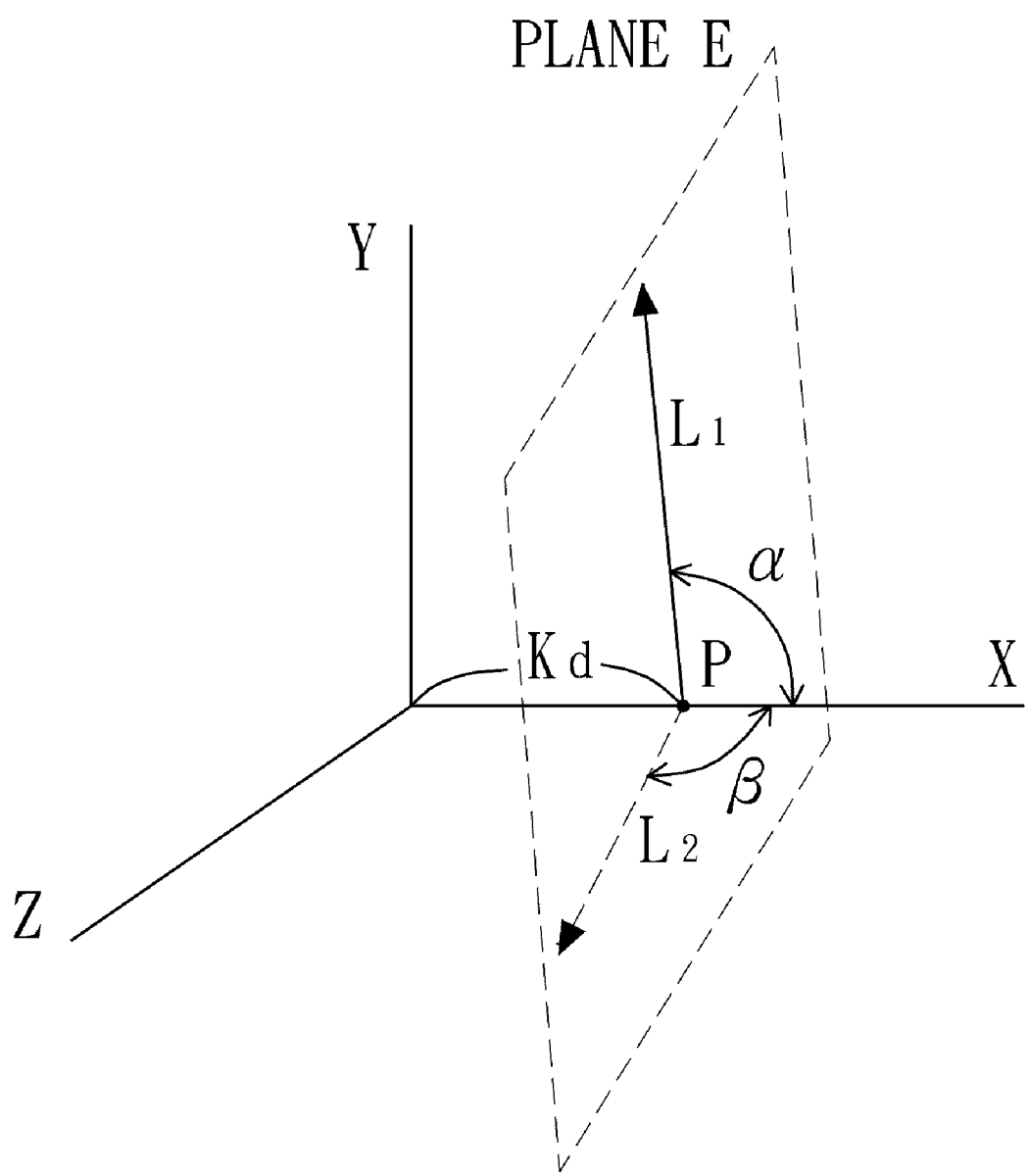
FIG. 4 is a diagram showing the step of constructing an optimal symmetry plane and its corresponding parameters in FIG. 3.
Figure 5:
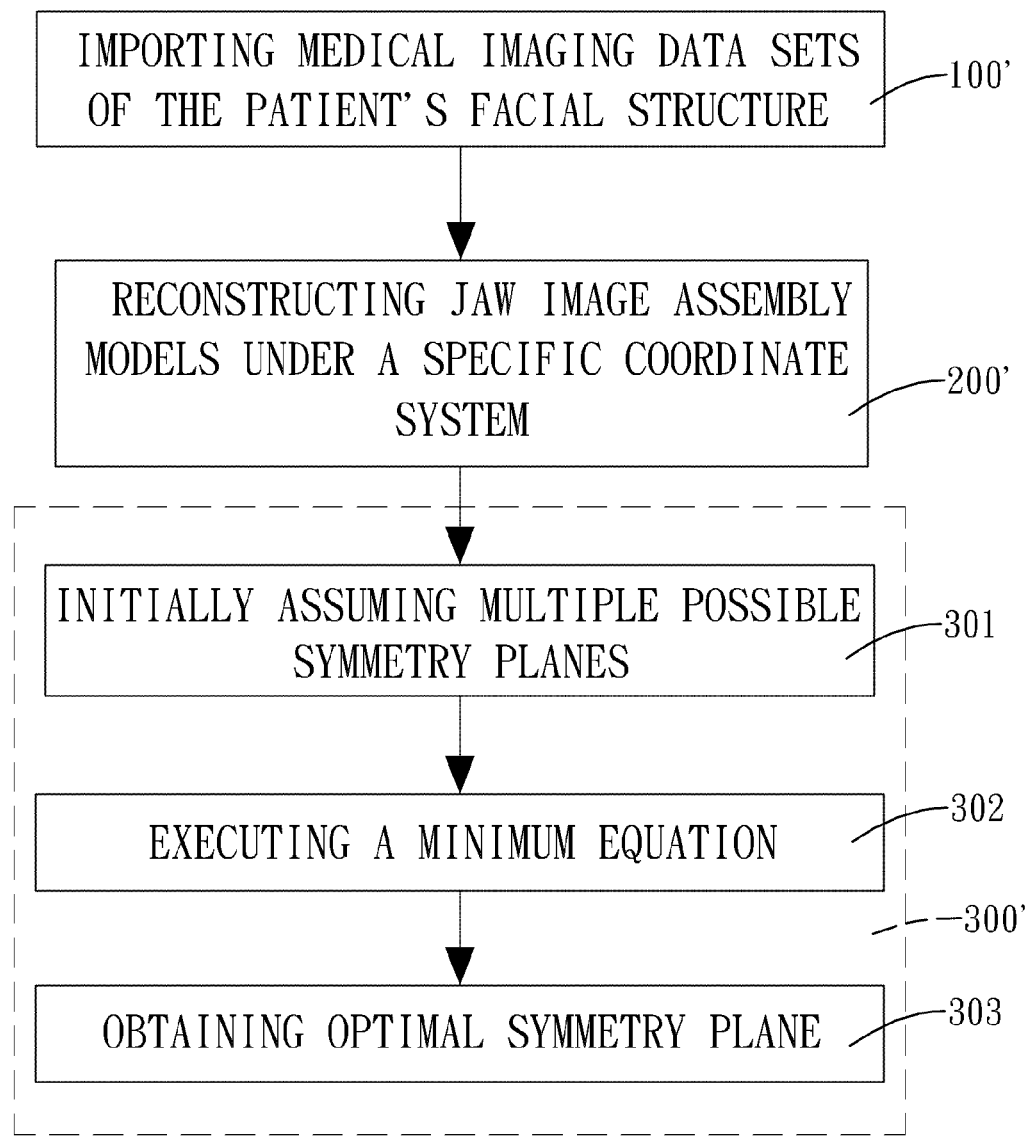
FIG. 5 is a flow chart of a second embodiment of the asymmetry quantifying process.

3. With reference to FIG. 4, $L_1$ is an intersection line between plane E and plane XY, $L_2$ is an intersection line between plane E and plane XZ, point P is an intersection point between the x-axis and the plane E, $\alpha$ is an angle between $L_1$ and the x-axis, $\beta$ is an angle between $L_2$ and the x-axis and $k_d$ is a distance between point P and the origin. Furthermore, the coordinates of point P are $(k_d,0,0)$, the direction vector of $L_1$ is $(\cos \alpha, \sin \alpha, 0)$, the direction vector of $L_2$ is $(\cos \beta, 0, \sin \beta)$ and the plane E has a vertical vector $(\cos \alpha, \sin \alpha, 0)*(\cos \beta, 0, \sin \beta) = (\sin \alpha \sin \beta, \sin \beta \cos \beta, \cos \beta \sin \alpha)$.

4. Therefore, $\alpha = \sin \alpha \sin \beta$, $b = \sin \beta \cos \beta$, $c = \cos \beta \sin \alpha$ and $d = -k_d(\sin \alpha \sin \beta)$, and further, the plane E can be simplified to $(\sin \alpha \sin \beta)x + (\sin \beta \cos \beta)y + (\cos \beta \sin \alpha)z - (\sin \alpha \sin \beta)k_d = 0$.

5. The error equation is defined as $$E(\alpha, \beta, k_d) = \left(\sum_{i=0}^{n-1}[f(x_i, y_i, z_i) - f(x_{si}, y_{si}, z_{si})]^2\right)/n.$$

6. Those binary image data sets generated from the step of image processing (202) are to be computed by the error equation and the error equation can be simplified into $$E(\alpha, \beta, k_d) = \left(\sum_{i=0}^{n-1}[f(x_i, y_i, z_i) \wedge f(x_{si}, y_{si}, z_{si})]\right)/n,$$

wherein $$f(x_i, y_i, z_i) \wedge f(x_{si}, y_{si}, z_{si}) = \begin{cases} 1, & f(x_i, y_i, z_i) = f(x_{si}, y_{si}, z_{si}) \\ 0, & f(x_i, y_i, z_i) \neq f(x_{si}, y_{si}, z_{si}). \end{cases}$$

Furthermore, a best symmetry value $E(\alpha, \beta, k_d)$ is obtained when parameters $\alpha$, $\beta$ and $k_d$ are the optimal parameters.

The step of constructing an optimal symmetry plane (500) comprises constructing an optimal symmetry plane associated with a best symmetry value and is performed as follows.

1. The optimal parameters $\alpha$, $\beta$ and $k_d$ are substituted into the equation $(\sin \alpha \sin \beta)x + (\sin \beta \cos \beta)y + (\cos \beta \sin \alpha)z - (\sin \alpha \sin \beta)k_d = 0$ of the symmetry plane obtained in the steps of executing an error equation (401) and obtaining the optimal parameters (402).

2. As the value of $f(x_i,y_i,z_i)\char`\^(x_{si},y_{si},z_{si})$ approaches to 1, the plane E is closer to optimal symmetry plane.

For example, the process analyzes the upper and lower jaw image assemblies in the jaw image assembly models and determines symmetry planes of the upper and lower jaw image assemblies in the jaw image assembly models.

Besides applying the method mentioned in the U.S. patent application Ser. No. 11/580,594, the asymmetry quantifying process may comprise steps of importing medical imaging data sets of the patient's facial structure (100'), reconstructing jaw image assembly models under a specific coordinate system (200') and obtaining an optimal symmetry plane (300').

The step of importing medical imaging data sets of the patient's facial structure (100') comprises importing medical imaging data sets of the patient's facial structure t into a computer. Each imaging data set comprises multiple image data. In an embodiment of the present invention, the medical imaging data sets are captured by computer tomography and are integrated into said jaw image model.

The step of reconstructing jaw image assembly models under a specific coordinate system (200') comprises reconstructing jaw image assembly models under a specific coordinate system in the computer. The specific coordinate system may be an orthogonal coordinate system, a spherical coordinate system or a cylindrical coordinate system.

The step of obtaining an optimal symmetry plane (300') comprises steps of initially assuming multiple possible symmetry planes (301), executing a minimum equation (302) and obtaining optimal symmetry plane (303).

Foregoing minimum equation is as follows $$\min_{a,b,c,d} f(a, b, c, d) = 1 - \frac{\sum_{P \in S}\begin{cases} 1, & P' \in S \\ 0, & P' \notin S \end{cases}}{\sum_{P \in S} 1},$$

wherein the assumed symmetry plane equation is E:$ax+by+cz+d=0$;

a normal vector of the assumed symmetry plane is $V \equiv (a\ b\ c)$;

a voxel of an image model S is P:$(x_i\ y_i\ z_i)$, P∈S; and a symmetry point of each voxel is $$P': (x'\ y'\ z') = P - 2V \frac{[P\ 1]\begin{bmatrix} V^T \\ d \end{bmatrix}}{\|V\|^2}.$$

Foregoing equation represents that counting the amount of the voxels, whose corresponding symmetry planes are confirmed to be belonged to the image model S, having the amount divided by the total number of voxels and subtracting the division value from 1. Since the division value is within 0 to 1, once the subtraction value is closer to zero, that means the assumed symmetry plane is nearly an optimal symmetry plane. Hence an optimal symmetry plane can be decided by determining which assumed symmetry plane has a minimum of subtraction value.

Because human's facial structure is not perfectly symmetric, therefore the present invention uses the process of quantifying asymmetry of the patient's facial structure in the jaw image assembly models to obtain an optimal symmetry plane as a reliable axis of symmetry. It is noted that the optimal symmetry plane of upper jaw is used as the midsagittal plane of the face for the mandible optimal symmetry plane to coincide with. With such method, we obtain two symmetry planes of the upper and lower jaw image assemblies, so as to compare overall asymmetry degree of patient's facial structure before and after dental casts adjustments to obtain the variation of the included angle and the specific distance between the symmetry planes of the upper and lower jaw image assemblies and determine if the overall symmetry degree is improved as predicted.

After symmetry analysis, for example, if included angle between the symmetry planes of the upper and lower jaw image assemblies increases or the asymmetry degree decreases, the surgical planning by transferring the x-ray cephalometric plan to plaster dental casts may carry manual errors and the planning process needs to be checked to find if any man-made mistake exists.

Figure 6A:
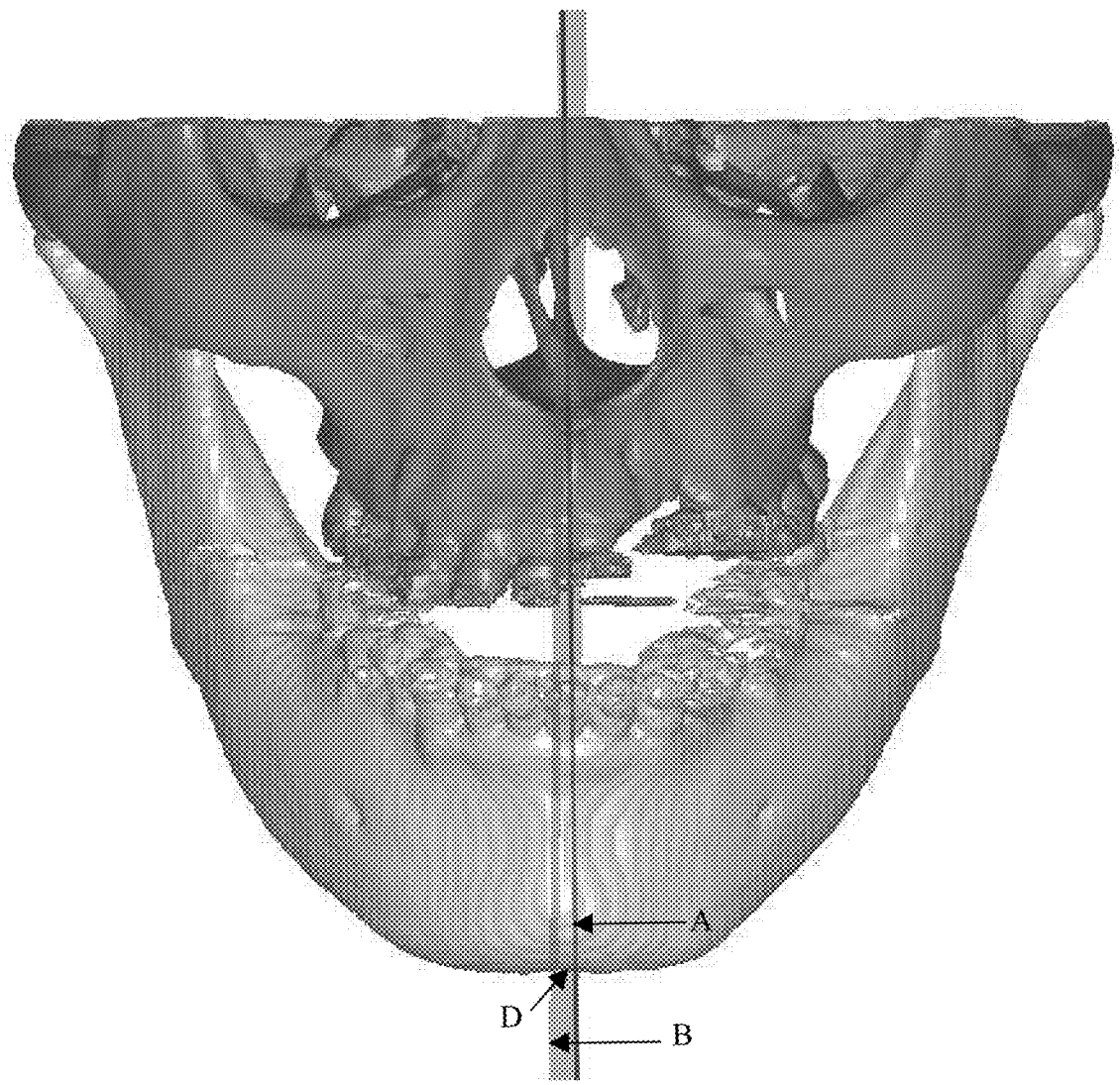
FIGS. 6a to 6d are computer-generated front, lateral, vertex and submental views of jaw image assembly models with symmetry planes before adjusting upper and lower jaw stone assemblies of a plaster dental cast, wherein an optimal symmetry plane of upper jaw image assembly is marked with A and was adjusted to parallel to observer's viewing direction (shown in one straight line in the projection drawing); an optimal symmetry plane of lower jaw image assembly is marked with B; and a specific distance between the optimal symmetry planes is marked with D.
Figure 6B:
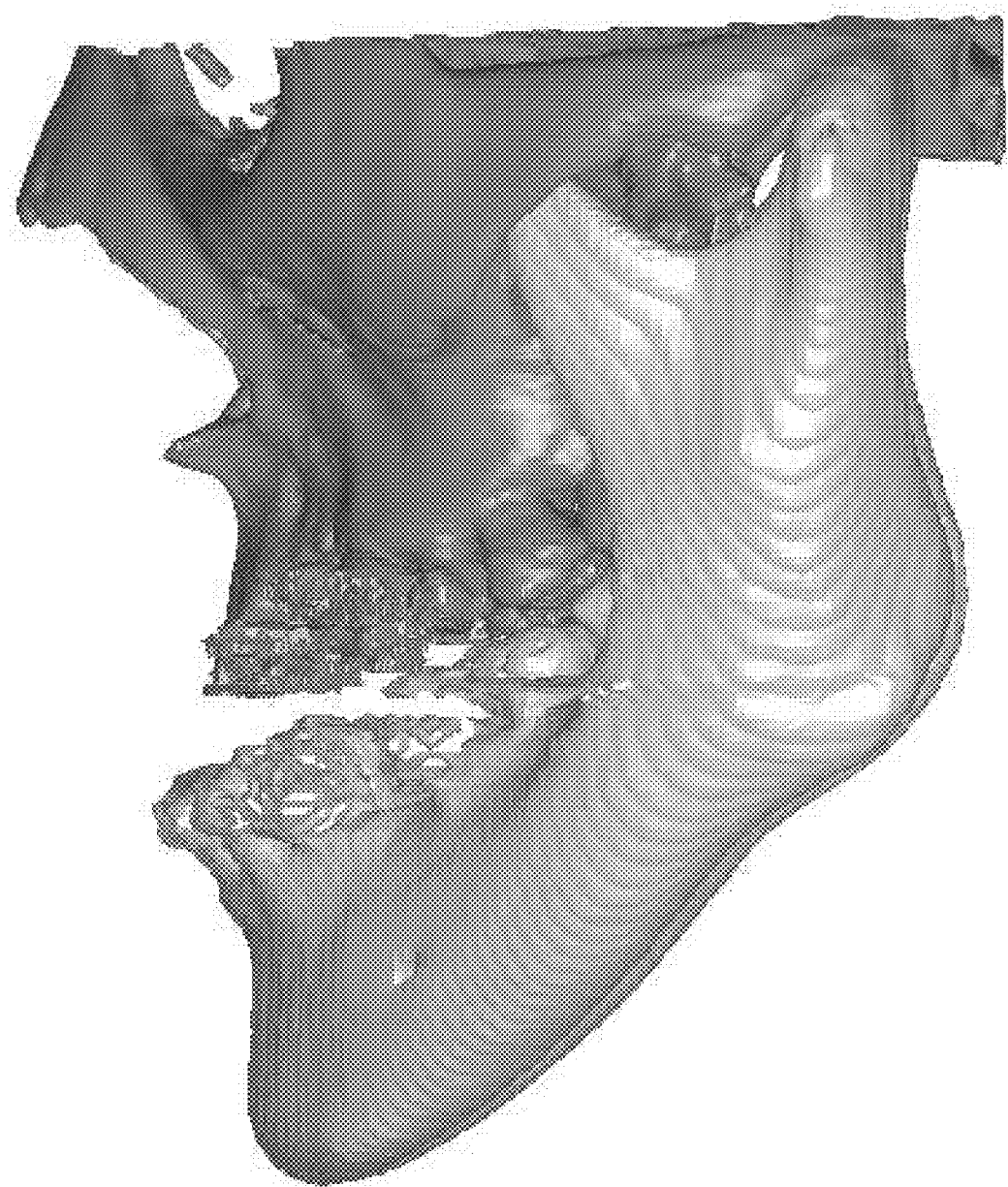
Figure 6C:
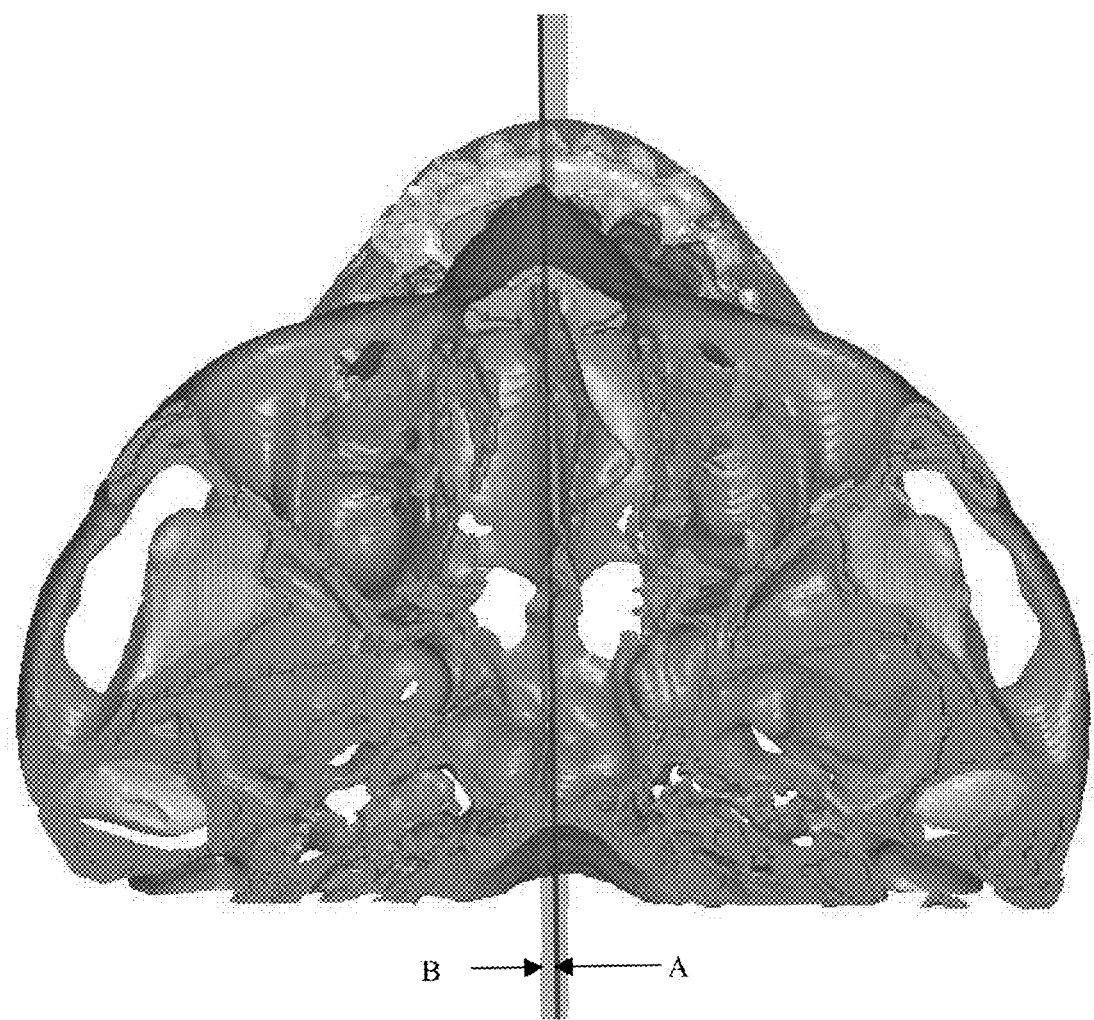
Figure 6D:
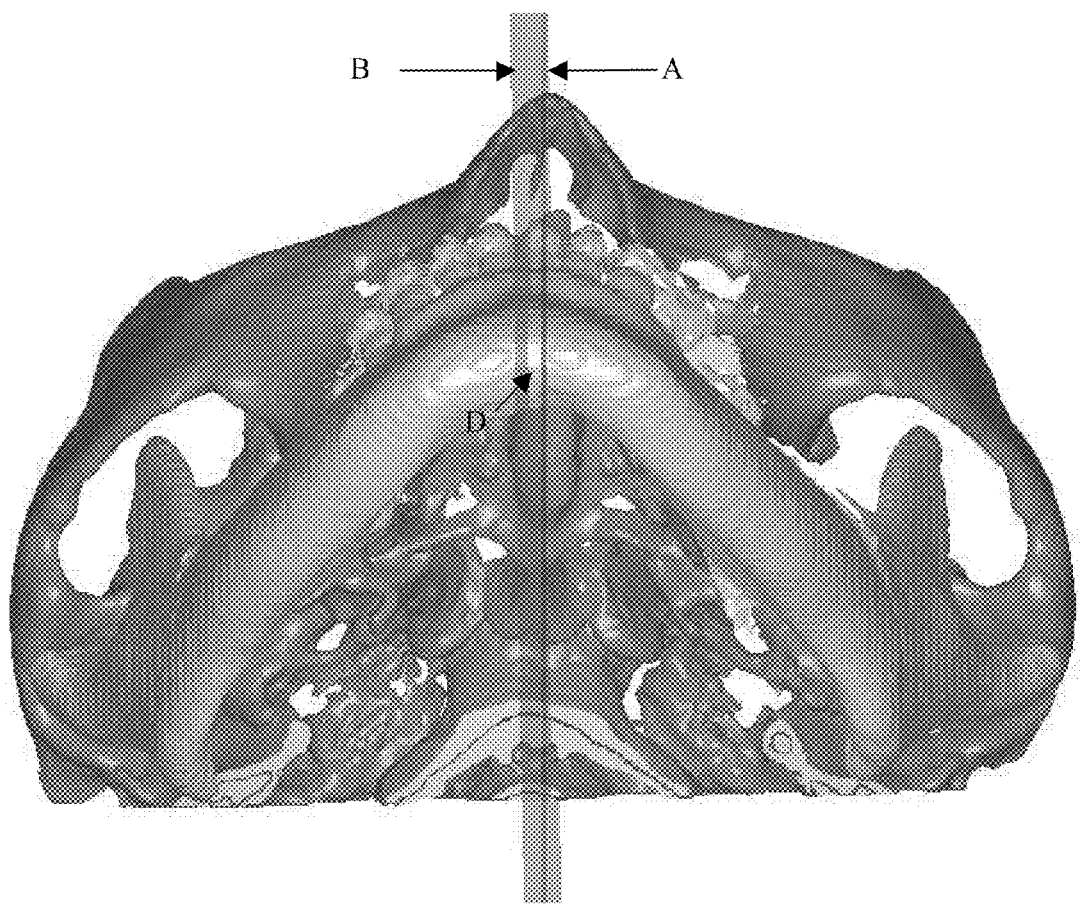

FIGS. 6(a) to 6(d) display jaw image assembly models having an upper jaw image assembly and a lower jaw image assembly each with symmetry planes (A)(B) in different views. FIG. 6(a) shows the degree of symmetry of the facial structure is fine from front view and the specific distance value D from the lowest point of symmetry plane (B) of the lower jaw image assembly to symmetry plane (A) of the upper jaw image assembly is maintained at a small value. But from a lateral view, FIG. 6(b) shows a mandibular prognathism case. A x-ray cephalometric plan is then made by the surgeon and infers a conclusion that the surgery only needs to move the lower jawbone backward. After executing a surgical planning on a plaster dental cast according to the x-ray cephalometric plan, corresponding post-surgical jaw image assembly models with symmetry planes (A)(B) are shown in FIGS. 7(a) to 7(d).

Figure 7A:
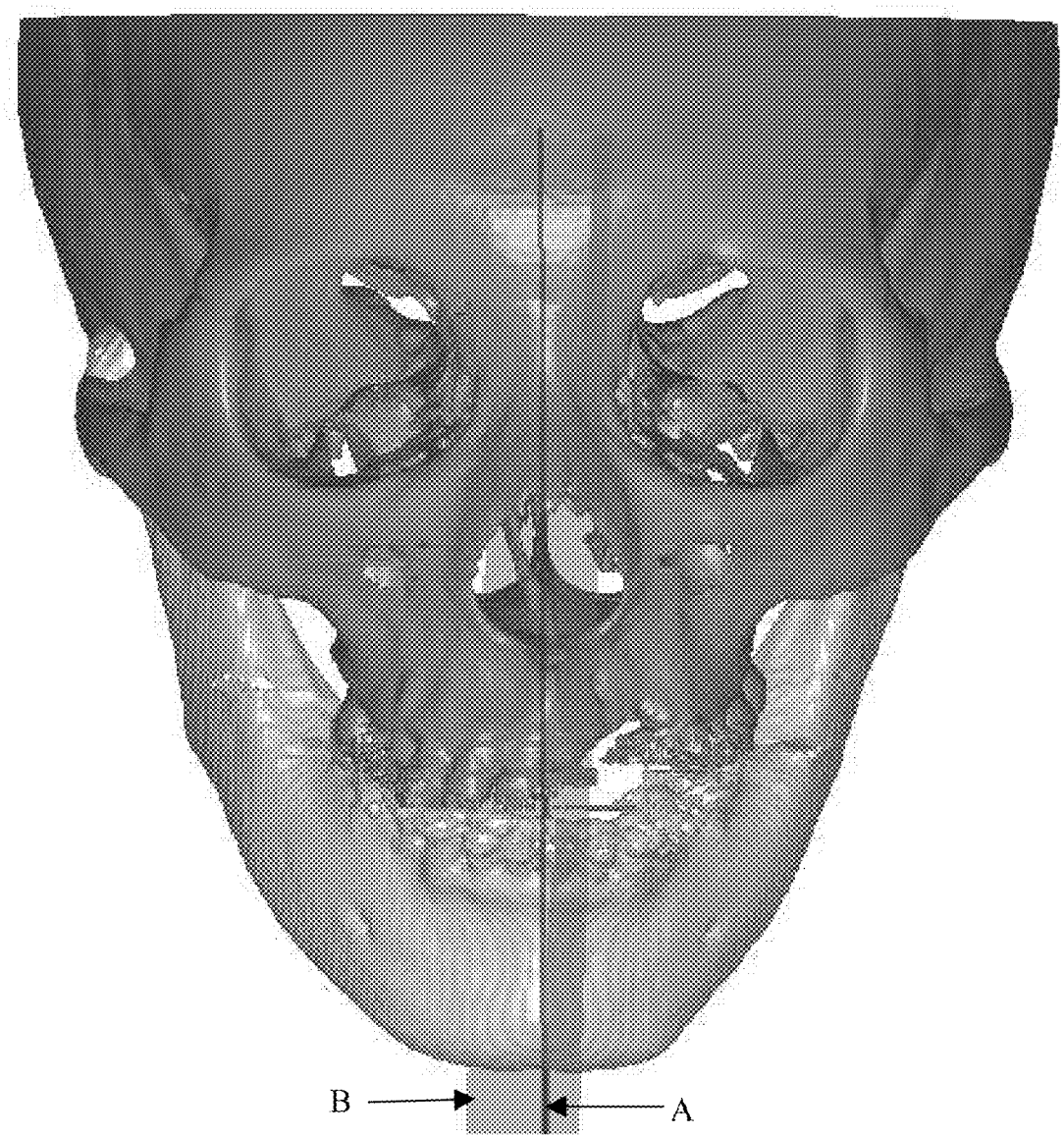
FIGS. 7a to 7d are computer-generated front, lateral, vertex and submental views of the jaw image assembly models after adjusting the upper and lower jaw stone assemblies of the plaster dental cast to predetermined positions based on a x-ray cephalometric plan, showing an asymmetric situation, wherein an optimal symmetry plane of upper jaw image assembly is marked with A and was adjusted to parallel to observer's viewing direction (shown in one straight line in the projection drawing); an optimal symmetry plane of lower jaw image assembly is marked with B; and a specific distance between the optimal symmetry planes is marked with D.
Figure 7B:
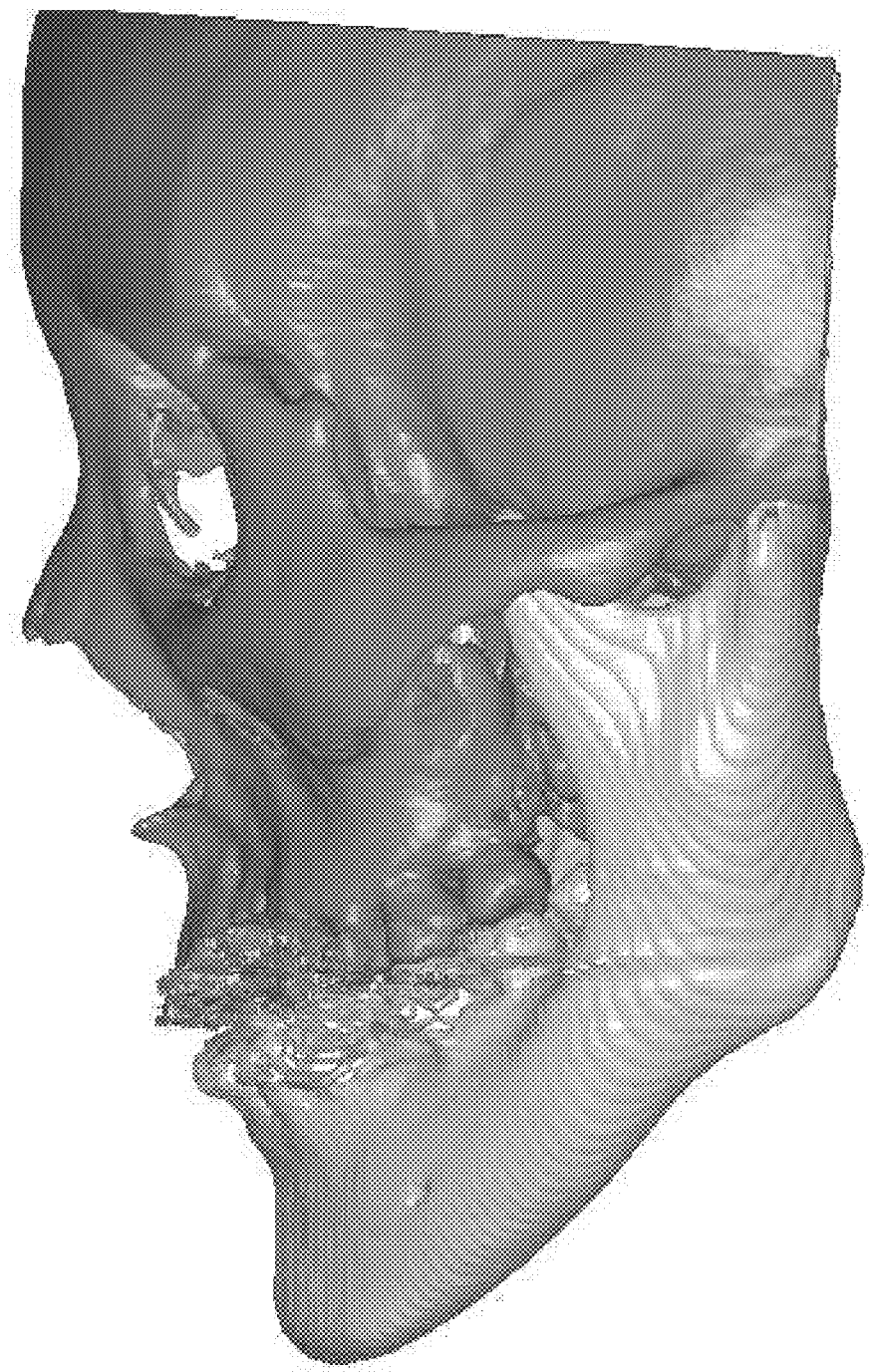
Figure 7C:
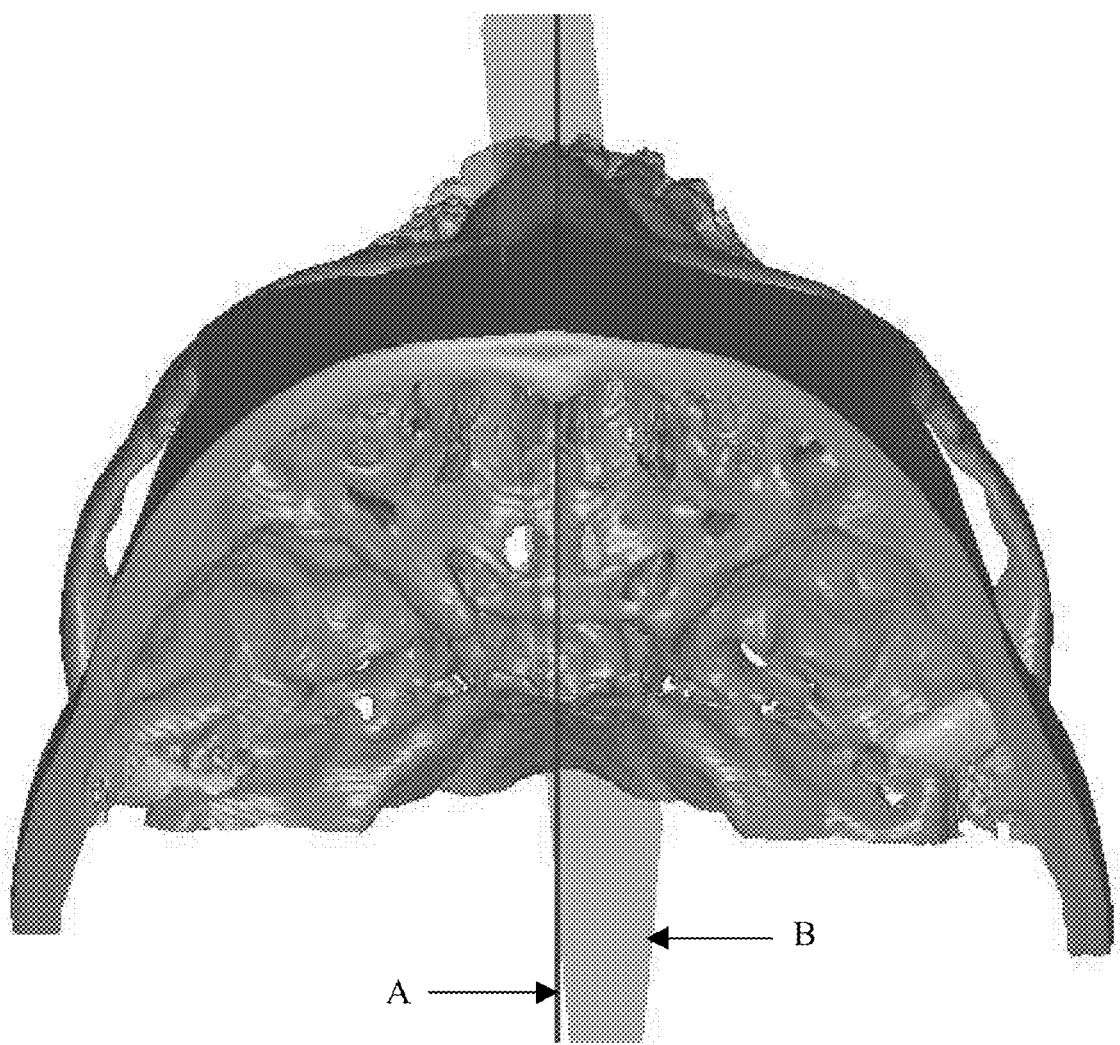
Figure 7D:
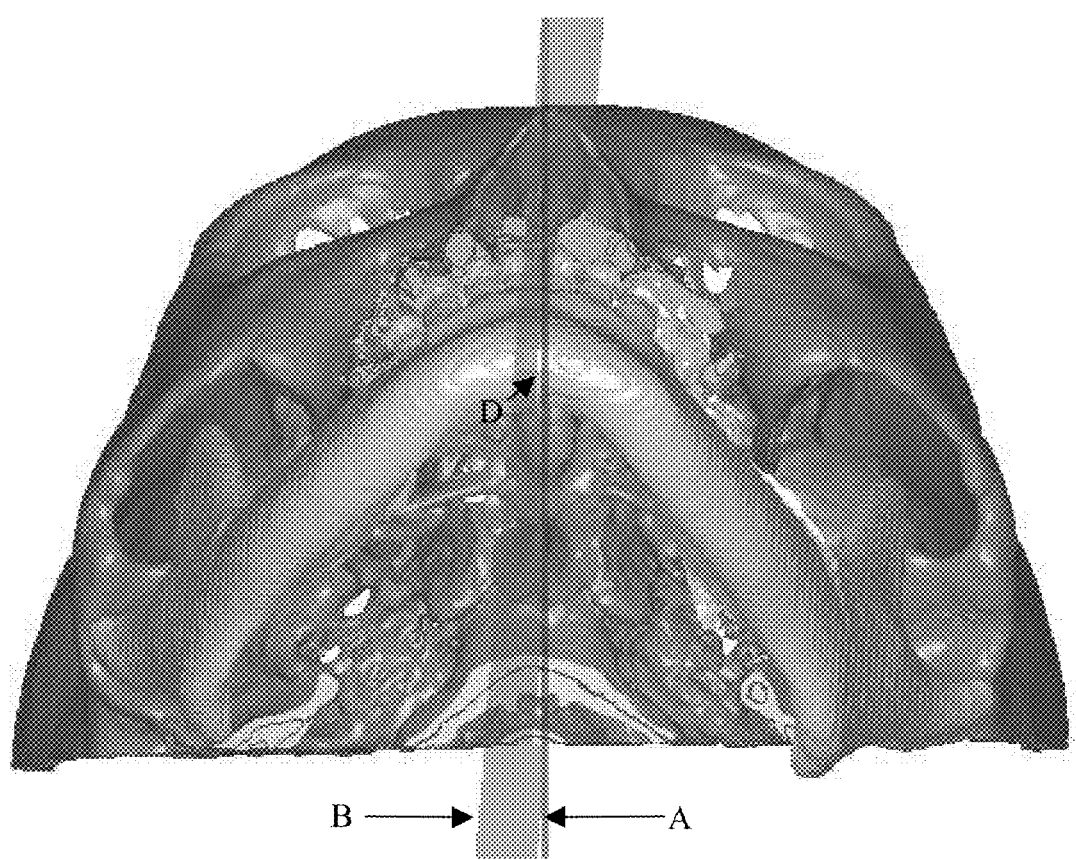
Figure 8A:
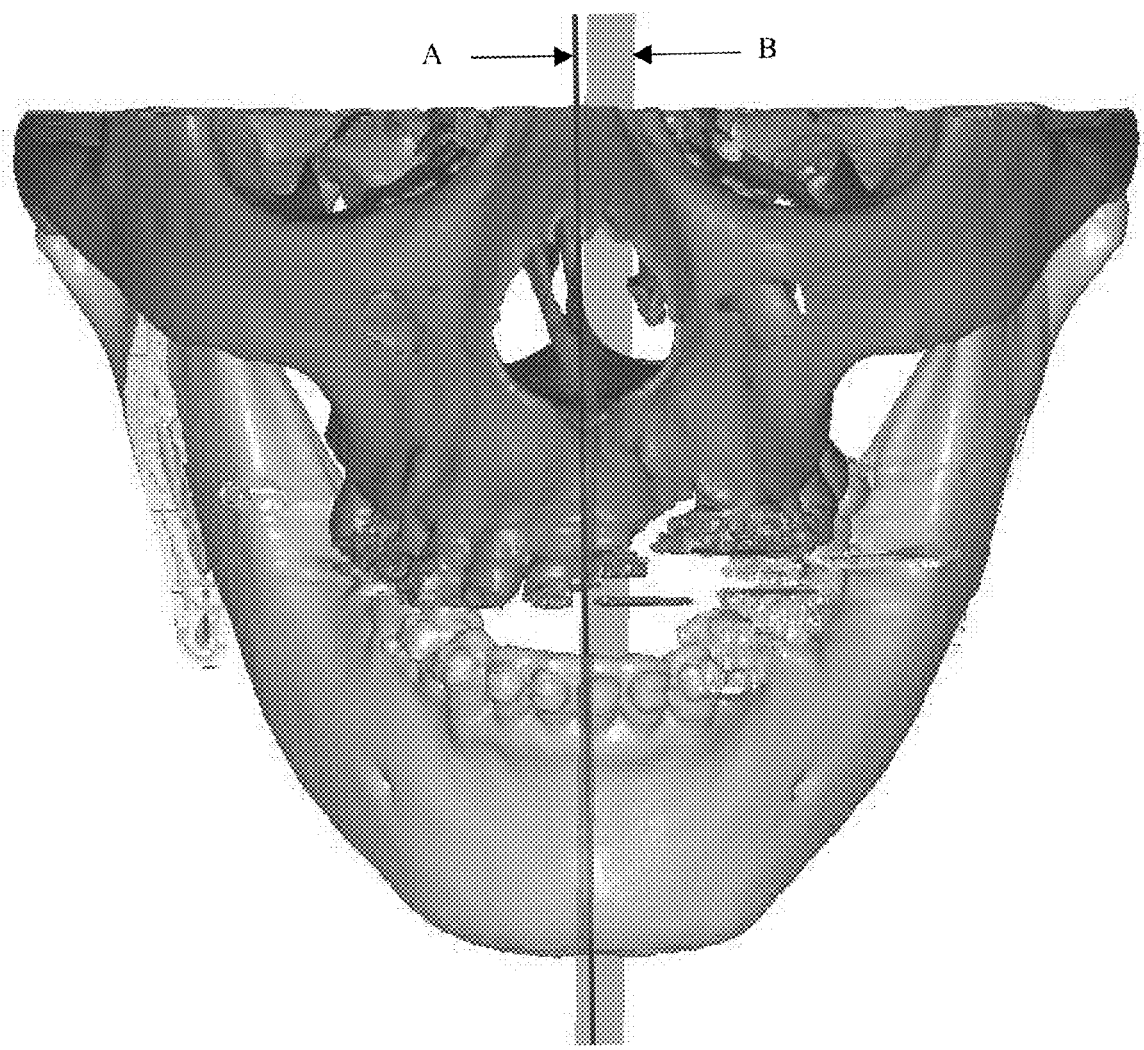
FIGS. 8a to 8d are computer-generated front, lateral, vertex and submental views of the jaw image assembly models after adjusting the upper and lower jaw stone assemblies of the plaster dental cast to predetermined positions based on a x-ray cephalometric plan, satisfying both occlusion function and facial aesthetic, wherein an optimal symmetry plane of upper jaw image assembly is marked with A and was adjusted to parallel to observer's viewing direction (shown in one straight line in the projection drawing); an optimal symmetry plane of lower jaw image assembly is marked with B; and a specific distance between the optimal symmetry planes is marked with D.
Figure 8B:
Figure 8C:
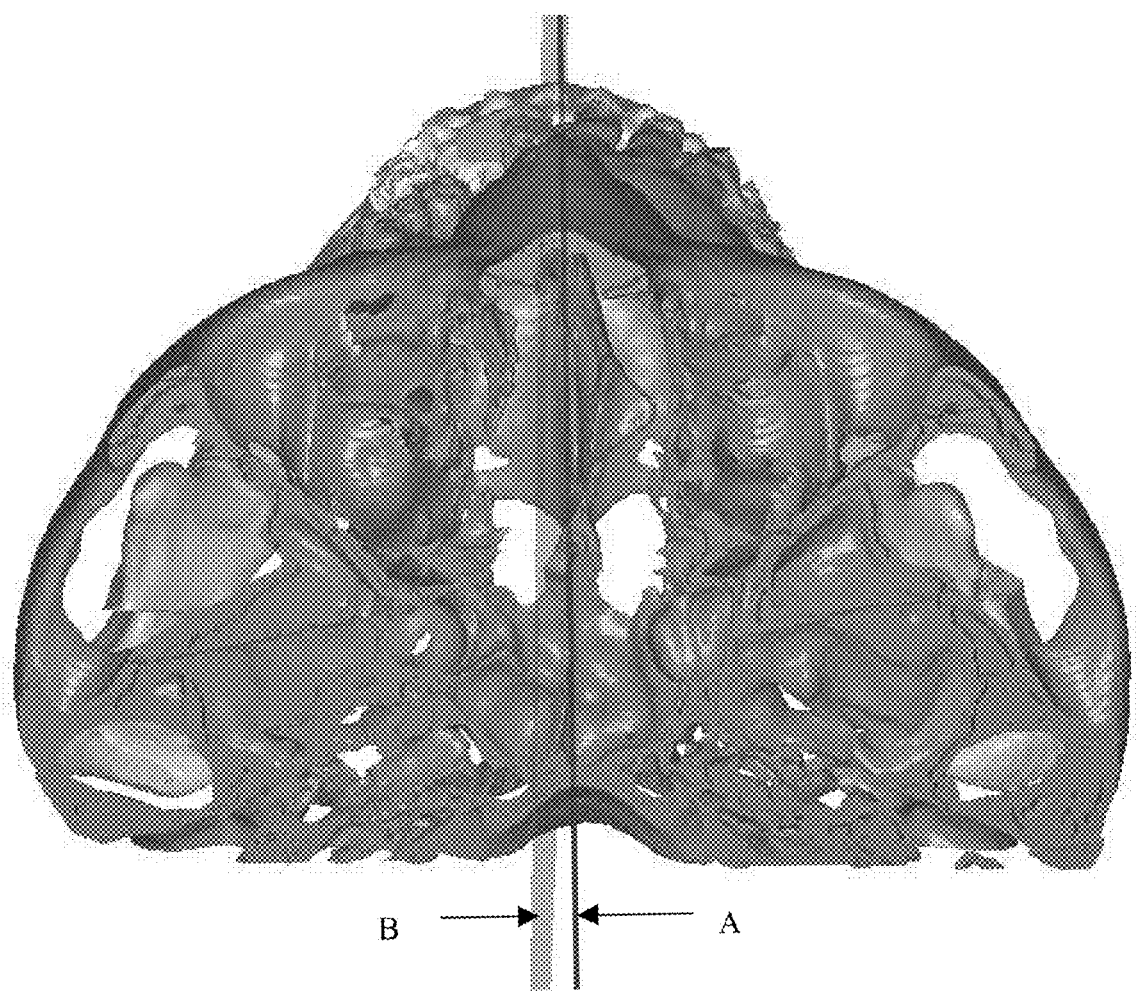
Figure 8D:
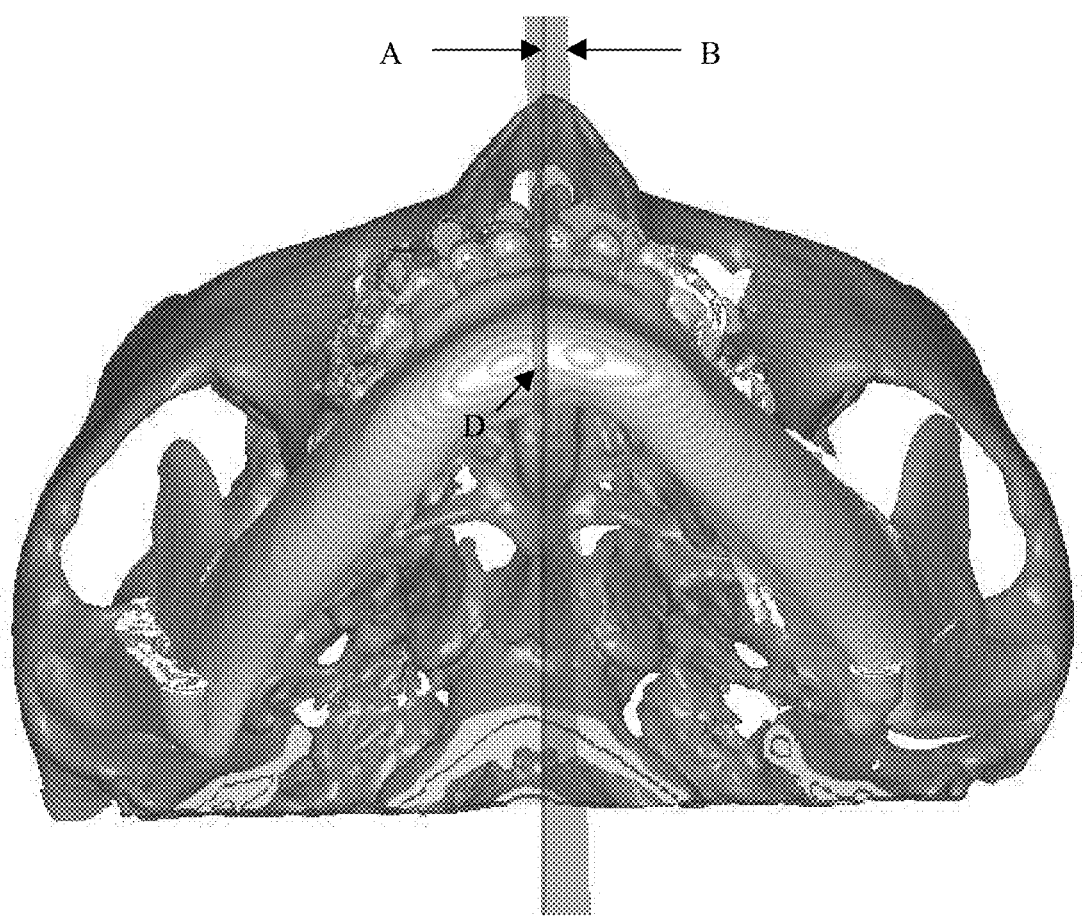

FIG. 7(c) shows the lower jaw image assembly was moved backward to a predetermined position, but from FIG. 7(a) and FIG. 7(b), the operation results the upper and lower jaw structures to a serious asymmetric situation. Further examination of the surgical simulation shows that the cut lower jaw image assembly was moved in a slant direction unexpectedly and caused the included angle between symmetry planes of the upper and lower jaw image assemblies increased. Therefore the method in accordance with the present invention indeed helps finding problems that cannot be predicted and fixed in advance in traditional surgical planning. With further reference to FIGS. 8a to 8d showing the post-surgical jaw image assembly models with symmetry planes (A)(B), it is obvious that the included angle is still maintained at a small value and so is the distance D. In FIG. 8b, the lower jaw image assembly was also moved to the predetermined position. Hence, with the help of the method of the present invention, the surgeon can compromises the occlusion function required by the x-ray cephalometric plan and the elevation of the degree of overall symmetry.

Such a method helps reconstructing 3D image models of patient's facial structure and performing registration to the patient's corresponding plaster dental cast. When executing a pre-surgical planning on the dental cast based on x-ray cephalometric plan, jaw image assembly models of the patient's facial structure can correspondingly and synchronously moved via a spatial tracking device. After the pre-surgical planning, the method uses symmetry analysis to estimate asymmetry degree and allows the surgeon to accordingly consider and adjust target positions of jaw stone assemblies in the per-surgical plan to meet both functional restoration and aesthetic requirements. Therefore the method assists a pre-surgical plan of an orthognathic surgery to be organized more deliberately and to achieve both occlusion function and facial symmetry.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A 3D planning and prediction method for optimizing facial skeleton symmetry in orthognathic surgery comprising steps of
making a plaster dental cast according to an oral cavity of a patient, wherein the plaster dental cast has an upper jaw stone assembly and a lower jaw stone assembly;
reconstructing jaw image assembly models in a computer by scanning the patient's facial structure using computer tomography, wherein the jaw image assembly models include an upper jaw image assembly and a lower jaw image assembly;
performing registration between the jaw image assembly models and the plaster dental cast, wherein a coordinate relationship between the virtual jaw image assembly models and the substantial plaster dental cast is established in the computer by coordinate transformation for position synchronization;
adjusting positions of the upper and lower jaw stone assemblies of the plaster dental cast to target positions according to a predetermined x-ray cephalometric plan;
tracking movements of the upper and low jaw stone assemblies with a spatial tracking device to synchronously and correspondingly reappear the same movements of the upper and lower jaw image assemblies to obtain a relative variation between positions of the upper and lower jaw image assemblies;
obtaining optimal symmetry planes of the upper and lower jaw image assemblies by a computer via an asymmetry quantifying process and thereby computing a variation of an included angle and a specific distance between the optimal symmetry planes of the upper and lower jaw image assemblies;
determining whether a degree of overall symmetry is elevated by determining whether the included angle and the specific distance are shortened under a condition of compromising the x-ray cephalometric plan, and recording the included angle and the specific distance and proceeding to next step when the degree of overall symmetry is elevated, otherwise checking if any error occurs while adjusting positions of the upper and low jaw stone assemblies of the plaster dental cast according to the x-ray cephalometric plan and returning to the step of tracking movements of the upper and low jaw stone assemblies of the plaster dental cast; and
making surgical occlusal splints according to the x-ray cephalometric plan and the recorded included angle and specific distance for surgical guiding.

2. The method as claimed in claim 1, wherein the spatial tracking device is selected from the group consisting of an optical tracking device, a mechanical tracking device, an ultrasonic tracking device, a gyroscope tracking device and an electromagnetic tracking device.

3. The method as claimed in claim 1, wherein the asymmetry quantifying process is operated in a computer and comprises steps of
importing medical imaging data sets of the patient's facial structure into a computer;
selecting regions of interest of the patient's facial structure in each medical imaging data set locating the regions of interest of the patient's facial structure in each medical imaging data set, and comprising steps of
selecting contrast and threshold arguments that both define the regions of interest of the patient's facial structure in each medical imaging data set; and
image processing using the contrast and threshold arguments to generate binary image data and locates the regions of interest of the patient's facial structure in each medical image data set;
processing those binary image data by executing an error equation and obtaining optimal parameters corresponding to the error equation; and
constructing an optimal symmetry plane with a best symmetry value, wherein the best symmetry value is a ratio value obtained from the error equation.

4. The method as claimed in claim 3, wherein the step of constructing an optimal symmetry plane further comprising steps of
assuming an equation $(\sin \alpha \sin \beta)x + (\sin \beta \cos \beta)y + (\cos \beta \sin \alpha)z - (\sin \alpha \sin \beta)k_d = 0$ being a symmetry plane of the patient's facial structure, wherein parameters $\alpha$, $\beta$ and $k_d$ are obtained from the step of obtaining the optimal parameters, $\alpha$ is an angle between an x-axis and an intersection line between the symmetry plane and the plane XY, $\beta$ is an angle between the x-axis and an intersection line between the symmetry plane and the plane XZ and $k_d$ is a distance between a point on the symmetry plane and the origin; and
obtaining the symmetry plane by substituting the optimal parameters $\alpha$, $\beta$ and $k_d$ into the equation $(\sin \alpha \sin \beta)x + (\sin \beta \cos \beta)y + (\cos \beta \sin \alpha)z - (\sin \alpha \sin \beta)k_d = 0$ of the symmetry plane.

5. The method as claimed in claim 4, wherein the step of processing the medical imaging data sets further comprises steps of
executing an error equation $$E(\alpha, \beta, k_d) = \left(\sum_{i=0}^{n-1} [f(x_i, y_i, z_i) \wedge f(x_{si}, y_{si}, z_{si})]\right) / n,$$

wherein $$f(x_i, y_i, z_i) \wedge f(x_{si}, y_{si}, z_{si}) = \begin{cases} 1, & f(x_i, y_i, z_i) = f(x_{si}, y_{si}, z_{si}) \\ 0, & f(x_i, y_i, z_i) \neq f(x_{si}, y_{si}, z_{si}); \end{cases}$$

and
obtaining the optimal parameters $\alpha$, $\beta$ and $k_d$ by executing the error equation.

6. The method as claimed in claim 1, wherein the asymmetry quantifying process is operated in a computer and comprises steps of
importing medical imaging data sets of the patient's facial structure into a computer;
reconstructing jaw image assembly models under a specific coordinate system by processing the medical image data in each data set; and
obtaining an optimal symmetry plane by initially assuming multiple possible symmetry planes, computing corresponding symmetry voxels of the image model relative to each assumed symmetry plane and taking an assumed symmetry plane that has the most symmetry voxels belonging to the image model as an optimal symmetry plane.

7. The method as claimed in claim 6, wherein the step of obtaining an optimal symmetry plane comprises a step of executing a minimum equation $$\min_{a,b,c,d} f(a,b,c,d) = 1 - \frac{\sum_{P \in S} \begin{cases} 1, & P' \in S \\ 0, & P' \notin S \end{cases}}{\sum_{P \in S} 1},$$

wherein the assumed symmetry plane equation is $E: ax+by+cz+d=0$;

a normal vector of the assumed symmetry plane is $V \equiv (a\ b\ c)$;

a voxel of the image model is $P:(x_i\ y_i\ z_i)$, $P \in S$; and a symmetry point of each voxel is $$P': (x'\ y'\ z') = P - 2V \frac{[P\ 1]\begin{bmatrix} V^T \\ d \end{bmatrix}}{\|V\|^2}.$$

8. The method as claimed in claim 6, wherein the specific coordinate system is selected from the group consisting of an orthogonal coordinate system, a spherical coordinate system and a cylindrical coordinate system.

9. The method as claimed in claim 1, wherein the plaster dental cast further has multiple tracking plates mounted on the upper and lower jaw stone assemblies, wherein each tracking plate has at least three recognition spots or at least two vector-based patterns.

10. The method as claimed in claim 9, wherein each tracking plate is attached with multiple light-emitting diodes.

11. The method as claimed in claim 9, wherein each tracking plate is attached with multiple reflection balls.

12. The method as claimed in claim 9, wherein each tracking plate has multiple recognized patterns.

* * * * *